(12) United States Patent
Leung et al.

(10) Patent No.: US 10,792,337 B2
(45) Date of Patent: Oct. 6, 2020

(54) WOUND HEALING COMPOSITIONS

(71) Applicant: KCI Licensing, Inc., San Antonio, TX (US)

(72) Inventors: Braden King-Fung Leung, San Antonio, TX (US); Ona Whelove, San Antonio, TX (US); Chester R. Edlund, San Antonio, TX (US); John R. Harper, Boerne, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1397 days.

(21) Appl. No.: 14/206,914

(22) Filed: Mar. 12, 2014

(65) Prior Publication Data

US 2014/0276493 A1   Sep. 18, 2014

Related U.S. Application Data

(60) Provisional application No. 61/799,367, filed on Mar. 15, 2013.

(51) Int. Cl.
*A61K 38/39* (2006.01)
*A61L 26/00* (2006.01)
(Continued)

(52) U.S. Cl.
CPC ........ *A61K 38/39* (2013.01); *A61F 13/00063* (2013.01); *A61F 13/00068* (2013.01);
(Continued)

(58) Field of Classification Search
CPC ...... A61K 38/39; A61K 9/004; A61K 31/085; A61K 31/14; A61K 31/155; A61K 31/201; A61K 31/7036; A61K 31/785; A61K 33/00; A61K 33/04; A61K 33/30; A61K 33/34; A61K 33/38; A61K 35/76; A61K 36/232; A61K 36/54; A61K 36/61; A61K 36/886; A61K 38/014; A61K 38/40; A61K 45/06; A61F 13/00063; A61F 13/00068;
(Continued)

(56) References Cited

U.S. PATENT DOCUMENTS 1,355,846 A   10/1920   Rannells
2,547,758 A   4/1951    Keeling
(Continued)

FOREIGN PATENT DOCUMENTS

AU   550575 A1   3/1986
AU   745271     4/1999
(Continued)

OTHER PUBLICATIONS

International Search Report and Written Opinion for corresponding PCT/US2014/025000 dated Jul. 1, 2014.
(Continued)

*Primary Examiner* — Andrew J Mensh

(57) ABSTRACT

Provided herein are biologically active solution compositions comprising one or more sacrificial proteolytic enzyme substrates, one or more preservatives, and one or more antimicrobial agents and methods of using the solution compositions to treat tissue sites, in particular chronic wounds. The compositions may be used in conjunction with negative pressure wound therapy to treat tissue sites.

35 Claims, 2 Drawing Sheets

(51) Int. Cl.

| | | |
|---|---|---|
| A61K 45/06 | (2006.01) | |
| A61M 1/00 | (2006.01) | |
| A61M 5/142 | (2006.01) | |
| A61F 13/00 | (2006.01) | |
| A61K 33/38 | (2006.01) | |
| A61K 38/01 | (2006.01) | |
| A61K 31/14 | (2006.01) | |
| A61K 33/30 | (2006.01) | |
| A61K 33/34 | (2006.01) | |
| A61K 31/201 | (2006.01) | |
| A61K 36/54 | (2006.01) | |
| A61K 31/155 | (2006.01) | |
| A61K 31/785 | (2006.01) | |
| A61K 33/00 | (2006.01) | |
| A61K 31/7036 | (2006.01) | |
| A61K 35/76 | (2015.01) | |
| A61K 36/61 | (2006.01) | |
| A61K 33/04 | (2006.01) | |
| A61K 36/232 | (2006.01) | |
| A61K 36/886 | (2006.01) | |
| A61K 9/00 | (2006.01) | |
| A61L 15/32 | (2006.01) | |
| A61K 31/085 | (2006.01) | |
| A61K 38/40 | (2006.01) | |
| A61L 15/42 | (2006.01) | |
| A61L 15/46 | (2006.01) | |

(52) U.S. Cl.
CPC .......... *A61K 9/0014* (2013.01); *A61K 31/085* (2013.01); *A61K 31/14* (2013.01); *A61K 31/155* (2013.01); *A61K 31/201* (2013.01); *A61K 31/7036* (2013.01); *A61K 31/785* (2013.01); *A61K 33/00* (2013.01); *A61K 33/04* (2013.01); *A61K 33/30* (2013.01); *A61K 33/34* (2013.01); *A61K 33/38* (2013.01); *A61K 35/76* (2013.01); *A61K 36/232* (2013.01); *A61K 36/54* (2013.01); *A61K 36/61* (2013.01); *A61K 36/886* (2013.01); *A61K 38/014* (2013.01); *A61K 38/40* (2013.01); *A61K 45/06* (2013.01); *A61L 15/325* (2013.01); *A61L 15/425* (2013.01); *A61L 15/46* (2013.01); *A61L 26/0033* (2013.01); *A61L 26/0066* (2013.01); *A61M 1/0088* (2013.01); *A61M 5/142* (2013.01)

(58) Field of Classification Search
CPC ...... A61L 15/325; A61L 15/425; A61L 15/46; A61L 26/0033; A61L 26/0066; A61M 1/0088; A61M 5/142
USPC ........................................................ 604/319
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A * | 5/1983 | Svedman .......... | A61F 13/00068 604/114 |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,035,687 A | 7/1991 | Sandbank | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,591,709 A | 1/1997 | Lindenbaum | |
| 5,607,388 A | 3/1997 | Ewall | |
| 5,636,643 A | 6/1997 | Argenta et al. | |
| 5,645,081 A | 7/1997 | Argenta et al. | |
| 5,679,697 A | 10/1997 | Garnett | |

(56) References Cited

U.S. PATENT DOCUMENTS

| | | | |
|---|---|---|---|
| 5,759,570 A | 6/1998 | Arnold | |
| 6,071,267 A | 6/2000 | Zamierowski | |
| 6,135,116 A | 10/2000 | Vogel et al. | |
| 6,166,084 A | 12/2000 | Bloor | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,814,097 B2 | 11/2004 | Girouard | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,563,799 B2 | 10/2013 | Kamakura et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0168400 A1 | 11/2002 | Jain | |
| 2003/0108587 A1 | 6/2003 | Orgill et al. | |
| 2004/0082925 A1* | 4/2004 | Patel | A61L 15/44 604/289 |
| 2004/0138103 A1 | 7/2004 | Patt | |
| 2005/0186260 A1 | 8/2005 | Narini et al. | |
| 2005/0281858 A1 | 12/2005 | Kloke et al. | |
| 2006/0034816 A1 | 2/2006 | Davis et al. | |
| 2006/0074108 A1* | 4/2006 | Gupta | A61K 31/4184 514/332 |
| 2006/0079852 A1 | 4/2006 | Bubb et al. | |
| 2006/0100586 A1 | 5/2006 | Karpowicz et al. | |
| 2006/0271104 A1 | 11/2006 | Viola et al. | |
| 2007/0055209 A1 | 3/2007 | Patel et al. | |
| 2007/0066946 A1 | 3/2007 | Haggstrom et al. | |
| 2007/0073210 A1 | 3/2007 | Hille et al. | |
| 2007/0128296 A1 | 6/2007 | Hoekstra et al. | |
| 2007/0149487 A1 | 6/2007 | Pang et al. | |
| 2007/0185426 A1 | 8/2007 | Ambrosio et al. | |
| 2007/0185463 A1 | 8/2007 | Mulligan | |
| 2007/0225663 A1 | 9/2007 | Watt et al. | |
| 2007/0237812 A1 | 10/2007 | Patel et al. | |
| 2007/0299410 A1 | 12/2007 | Eknoian et al. | |
| 2008/0260808 A1 | 10/2008 | Pinna et al. | |
| 2008/0275409 A1 | 11/2008 | Kane et al. | |
| 2009/0035289 A1* | 2/2009 | Wagner | A01N 1/0221 424/93.72 |
| 2009/0157017 A1 | 6/2009 | Ambrosio | |
| 2009/0177133 A1 | 7/2009 | Kieswetter et al. | |
| 2009/0220450 A1 | 9/2009 | Green et al. | |
| 2009/0280162 A1 | 11/2009 | Wegmann et al. | |
| 2010/0249733 A9 | 9/2010 | Blott et al. | |
| 2010/0255109 A1 | 10/2010 | Kim et al. | |
| 2010/0260823 A1* | 10/2010 | Alupei | A61K 38/39 424/445 |
| 2010/0278784 A1 | 11/2010 | Pojasek et al. | |
| 2011/0213022 A1 | 9/2011 | Nelson | |
| 2011/0251566 A1 | 10/2011 | Zimnitsky et al. | |
| 2011/0306755 A1* | 12/2011 | Bhatia | A61K 38/39 530/356 |
| 2012/0245540 A1 | 9/2012 | Zimnitsky et al. | |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 102006038252 A1 | 2/2008 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 801170 A | 9/1958 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | 2005-132725 A | 5/2005 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/10808 A1 | 3/1997 |
| WO | 97/18007 | 5/1997 |
| WO | 99/13793 | 3/1999 |
| WO | 0024378 A1 | 5/2000 |
| WO | 0059424 A1 | 10/2000 |
| WO | 0100157 A1 | 1/2001 |
| WO | 02/085386 A2 | 10/2002 |
| WO | 2006034568 A1 | 4/2006 |
| WO | 2006/058318 A2 | 6/2006 |
| WO | 2006/095193 A2 | 9/2006 |
| WO | 2007092405 A2 | 8/2007 |
| WO | 2007/106590 A2 | 9/2007 |
| WO | 2008057600 A2 | 5/2008 |
| WO | 2008091521 A2 | 7/2008 |
| WO | 2008142569 A2 | 11/2008 |
| WO | 2009/088926 A1 | 7/2009 |
| WO | 2009137074 A1 | 11/2009 |
| WO | 2009158500 A2 | 12/2009 |
| WO | 2010017282 A1 | 2/2010 |
| WO | 2012162098 A2 | 11/2012 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998,

(56) References Cited

OTHER PUBLICATIONS vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
Alleva R et al: "alpha-Lipoic acid supplementation inhibits oxidative damage, accelerating chronic wound healing in patients undergoing hyperbaric oxygen therapy," Biochemical and Biophysical Research Communications, Academic Press, Inc. Orlando, FL, US, vol. 333, No. 2, Jul. 29, 2005, pp. 404-410, XP027229880, ISSN:0006-291X.
International Preliminary Report on Patentability for PCT/US2011/031441 dated Aug. 4, 2015.
Supplementary European Search Report for corresponding European Application No. EP08869720 dated Nov. 23, 2012.
Alpha Lipoic Acid 200 mg; http://www.seacoast.com/supplement/natural-factors-alpha-lipoic-acid-200-m-60-caps-13; viewed Mar. 30, 2011.
Inoguchi, T, et al., ""Protein Kinase C-Dependent Increase in Reactive Oxygen Species (ROS) Production in Vascular Tissues of Diabetes: Role of Vascular NAT(P)H Oxidase"" J Am Nephr 227-232 (2003).
James et al., "Antioxidant Characteristics of Chronic Wound Fluid" BR J Dermatol 145(1):185-6 (2001).
James et al., "Evidence of Oxidative Stress in Chronic Venous Ulcers" Wound Repair Regen 11(3):172-6 (2003).
Mendez, et al., "Fibroblasts Cultured from Venous Ulcers Display Cellular Characteristics of Senescence" J Vasc Surg 28(5): 876-83 (1998).
Novo, "Redox Mechanisms in Hepatic Chronic Wound Healing and Fibrogenesis" Fibrosenesis Tissue Repair 1 (1):5 (2008).
Rojas "Patients with Chronic Leg Ulcers Show Diminished Levels of Vitamins A and E, Carotenes and Zinc" Dermatol Surg 25(8):601-4 (1999).
Wlaschek "Oxidative Stress in Chronic Venous Leg Ulcers" Wound Repari Regen 13(5):452-61 (2005).
Eming "Inflammation in Wound Repair: Molecular and Cellular Mechanisms" Journal of Investigative Dermatology (2007).

(56) References Cited

OTHER PUBLICATIONS

Yager "Wound Fluids from Human Pressure Ulcers Contain Elevated Matrix Metalloproteinase Levels and Activity Compared to Surgical Wound Fluids" The Society for Investigative Dermatology 2006; 107(15): 744-748.

Sarisoezen "The Effects of Vitamins E and C on Fracture Healing in Rats" The Journal of International Medical Research 2002; 30:309-313.

Gray "Does Vitamin C Supplementation Promote Pressure Ulcer Healing:" J WOCN 2003; 30:245-9.

Jagetia "Ascorbic Acid Increases Healing of Excision Wounds of Mice Whole Body Exposed to Different Doses of G-Radiation" Burns 33 (2007) 484-494.

Lim "Dietary Supplementation of N-acetylcysteine Enhances Early Inflammatory Response During Cutaneous Wound Healing in Protein Malnourished Mice" Journal of Nutritional Biochemistry 17 (2006) 328-336.

Cardoso et al "Influence of Topical Administration of n-3 and n-6 Essential and n-9 Nonessential Fatty Acids on the Healing of Cutaneous Wounds" Wound Repair and Regeneration, 2004; 12-235-243.

Henriksen, Exercise Training and the Antioxidant alpha-lipoic Acid in the Treatment of Insulin Resistance and Type 2 Diabetes Free Radic Biol Med 2006 40(1):3-12.

Ames "Delaying the Mitochondrial Decay of Aging with Acetylcarnitine" Ann NY Acad Sci 2004 1033:108-116.

Holmquist "Lipoic Acid as a Novel Treatment for Alzheimer's Disease and Related Dementias" Pharmacology & Therapeutics 113 1 (2007): 154-164.

Kofuji "Stabilization of a-lipoic Acid by Complex Formation with Chitosan" Food Chemistry 2008; 109:167-171.

Alleva, et al., "a-Lipoic Acid Modulates Extracellular Matrix and Angiogenesis Gene Expression in Non-Healing Wounds Treated with Hyperbaric Oxygen Therapy." Mol Med 14 (3-4) 175-183.

Frank et al. "Large induction of the chemotactic cytokine RANTES during cutaneous wound repair: a regulatory role for nitric oxide in keratinocyte-derived RANTES expression," Biochem J. (2000) 347, (pp. 265-273) (9 pages).

Witte, et al., "Nitric oxide enhances experimental wound healing in diabetes," British Journal of Surgery 2002, 89 (pp. 1594-1601) (8 pages).

Lee et al, "Impaired wound healing and angiogenesis in eNOS-deficient mice," The American Physiological Society 1999/Am J. Physiol Heart Circ Physiol 277:1600-1608, 1999. (10 pages).

Najjar et al., "Evaluation of Poly-N-Acetyl Glucosamine as a Hemostatic Agent in Patients Undergoing Cardiac Catheterization: A Double-Blind Randomized Study," The Journal of TRAUMA®, Injury, Infection, and Critical Care; Jul. 2004 (Supplement) (4 pages).

Musalmah et al., "Effect of vitamin E on plasma malondialdehyde, antioxidant enzyme levels and the rates of wound closures during wound healing in normal and diabetic rats," Asia Pacific J. Clin Nutr (2002) 11 (Suppl): S448-S451 (4 pages).

Boykin, Jr. et al., "Diabetes-Impaired Wound Healing Predicted by Urinary Nitrate Assay—A Preliminary, Retrospective Study," available online at URL: http://www.hitechno.com/Final/links/DB.htm>; Wounds 11(3): 62-69, 1999 Health Management Publications, Inc. (8 pages).

International Search Report and Written Opinion dated Feb. 17, 2009; PCT Application No. PCT/US2008/088636.

Lateef et al., "Pretreatment of diabetic rats with lipoic acid improves healing of subsequently-induced abrasion wounds", Arch Dermatol Res (2005) 297:75-83 DOI 10.1007/s00403-005-0576-6. (9 pages).

International Search Report and Written Opinion dated Jun. 9, 2011; International PCT Application No. PCT/US2011/031441.

European Examination Report for related application 11715141.5, dated May 4, 2018.

European Examination Report for related application 14720324.4, dated Sep. 20, 2018.

De Paula et al, "Physical and Chemical Characterization of Poly(hexamethylene biguanide) Hydrochloride," 2011, 928-941.

Office Action for related U.S. Appl. No. 14/883,483, dated Aug. 20, 2019.

* cited by examiner

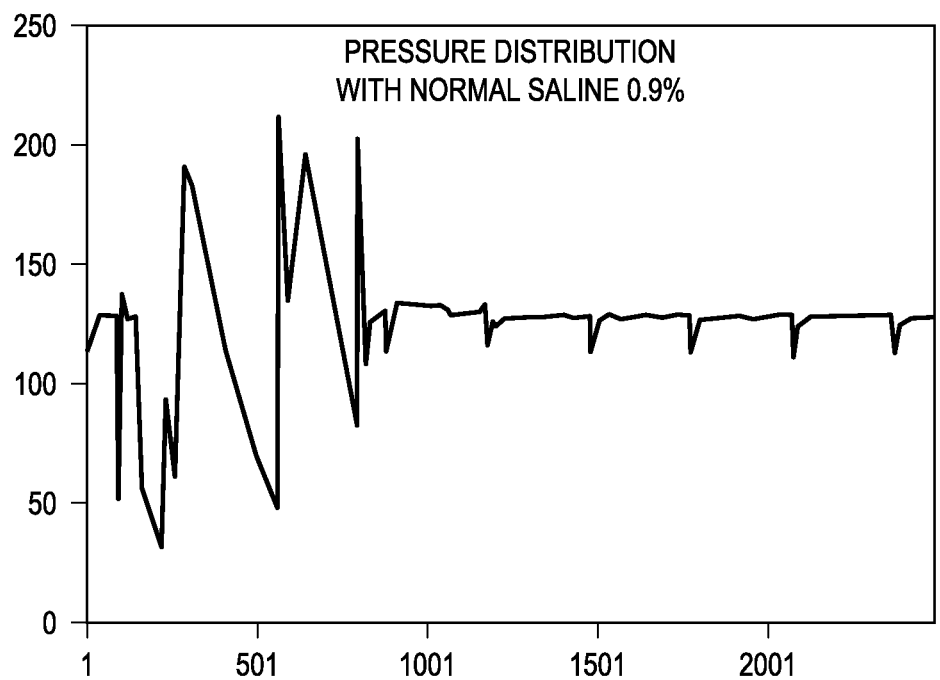
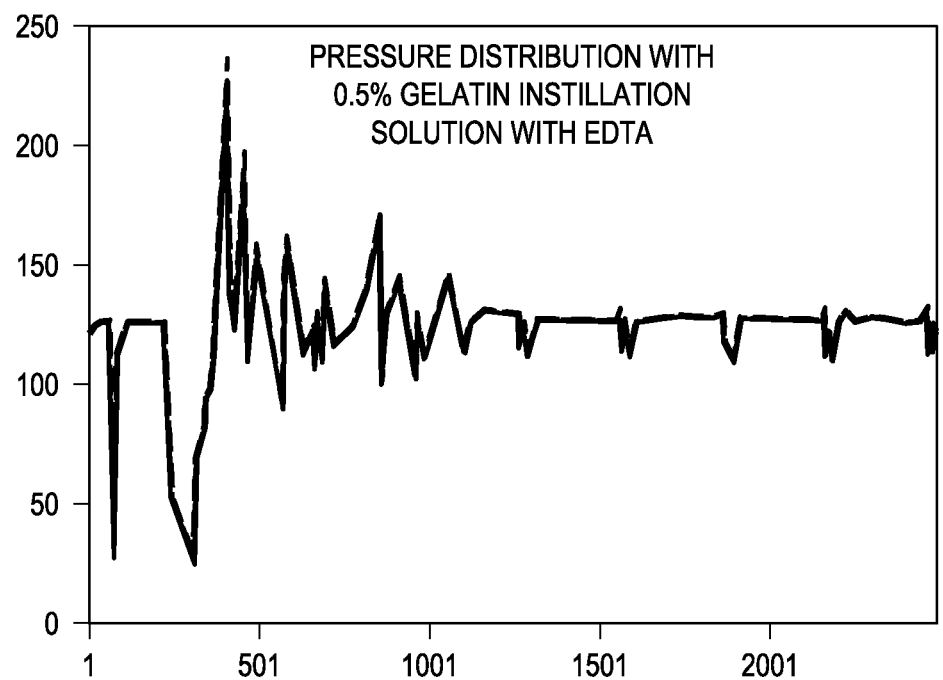

WOUND HEALING COMPOSITIONS

RELATED APPLICATION

The present invention claims the benefit, under 35 USC § 119(e), of the filing of U.S. Provisional Patent Application Ser. No. 61/799,367, entitled "WOUND HEALING COMPOSITIONS," filed Mar. 15, 2013, which is incorporated herein by reference for all purposes.

FIELD

The present disclosure relates generally to compositions and methods for medical treatment of wounds, and more particularly but without limitation, for treatment or prophylaxis of chronic wounds.

BACKGROUND

Typical procedures for treating chronic wounds such as, for example, venous ulcers, diabetic ulcers and pressure sores, include the use of absorbent dressings or hydrocolloid gels. Additionally, since most chronic wounds are infected, many wound dressings contain antimicrobial agents, such as silver or iodine, to either create a barrier to microorganisms or reduce microbial load. These treatments are used more for managing the wound environment and moisture balance than actively promoting wound healing.

In wound healing, the extracellular matrix (ECM), comprised largely of collagen, plays a significant role in the healing response. Chronic wounds suffer from the fact that increased levels of inflammatory cells and proteases are present and work to degrade the ECM, therefore inhibiting its healing. Matrix metalloproteases (MMPs) are among the proteases present in both acute and chronic wounds and play an important role in the wound healing response. In normal wound healing, MMPs help to degrade denatured ECM, which allows the functional matrix to be exposed. However, in chronic wounds, elevated numbers of MMPs and a resulting distortion in the ratio of MMPs to their inhibitors (tissue inhibitor metalloproteinase (TIMPs)) cause disruption in the wound healing system and can result in destruction of the ECM, growth factors, and granulation tissue.

The production of MMPs at a chronic wound site can be inhibited by preventing activation of MMPs or by use of MMP inhibitors. A sacrificial substrate for the MMPs can also be employed to inhibit production. Some wound dressings on the market use various forms of natural collagen as a sacrificial substrate for MMPs because the collagen also provides the mechanical properties (integrity) necessary to form the dressing. However, with the loss of the collagen over time, the sacrificial substrate is no longer available. Accordingly, managing wounds and other tissue sites with elevated levels of MMPs continues to present a significant challenge to healthcare providers and manufacturers.

SUMMARY

Described herein are bioactive compositions for treating tissue sites, in particular chronic wounds. The compositions described herein may comprise one or more sacrificial proteolytic enzyme substrates and one or more antimicrobial agents. The compositions may be solutions. As an illustrative embodiment, the solution compositions disclosed herein can consist essentially of one or more MMP substrates, one or more antimicrobial agents, and one or more preservatives such as sodium benzoate or chelators such as ethylenediaminetetraacetic acid (EDTA).

In one illustrative embodiment, the compositions are provided in a dispensable liquid form, suited for instillation, for the management of a tissue site through maintaining a moist wound bed along with the added benefit of MMP scavenging ability and antimicrobial effectiveness. This is an advancement over known methods and systems as a fresh batch of MMP substrate can be continually or cyclically delivered to a tissue site during each instillation.

BRIEF DESCRIPTION OF THE DRAWINGS

FIGS. 3A and 3B show that the bioactive composition of FIG. 2 performs similarly as a normal saline (0.9% NaCl) solution with a negative pressure wound therapy (NPWT) system. No degradation of the negative pressure was seen once the system stabilizes from the instill cycle seen by the initial peaks up to 1000 second time point.

DETAILED DESCRIPTION

Figure 1:
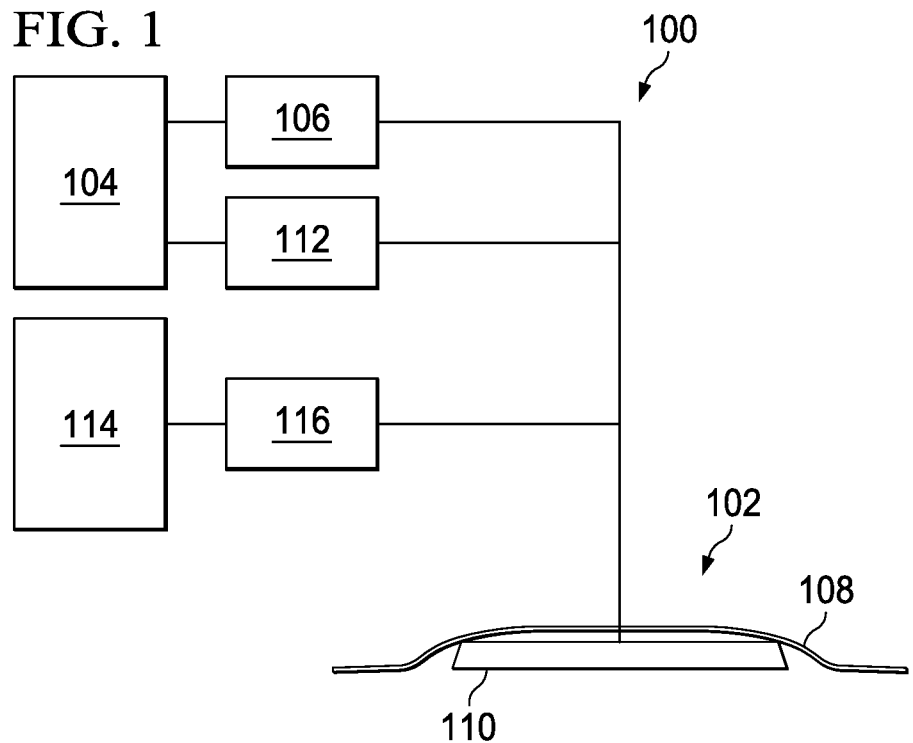
FIG. 1 shows a block diagram of a representative embodiment of a therapy system.

In the following detailed description of the illustrative embodiments, reference is made to the accompanying drawings that form a part hereof. These embodiments are described in sufficient detail to enable those skilled in the art to practice the compositions and methods disclosed herein, and it is understood that other embodiments may be utilized and that logical structural, mechanical, electrical, and chemical changes may be made without departing from the spirit or scope of the disclosure. To avoid detail not necessary to enable those skilled in the art to practice the embodiments described herein, the description may omit certain information known to those skilled in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

As presented herein, a bioactive composition in the form of a gelatin-based solution can competitively inhibit MMP activity, and the composition in the form of a solution can be used as an instillant to cleanse wounds. The combination of a MMP substrate and an antimicrobial agent in a dispensable liquid form, suited for instillation, enables the management of a tissue site through maintaining a moist wound bed in addition to providing MMP scavenging ability and antimicrobial effectiveness. To further promote healing and growth of tissue, embodiments of bioactive compositions including a preservative such as a chelator, for example EDTA, and an antimicrobial agent, may work synergistically to kill microbes while preventing further biofilm formation. This combination of the MMP substrate and antimicrobial agent can create an optimal wound healing environment, allowing for mitigation of prolonged inflammation due mainly to excessive proteases present at the tissue site and for progression into a normalized healing state. Also described herein is an innovative method of applying fresh sacrificial MMP substrate to the tissue site, while moisturizing and cleansing the tissue with a fresh batch of antimicrobial agent at every cycle of instillation.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include, for example, chronic, acute, traumatic, sub-acute, and dehisced wounds, partial-thickness burns, ulcers (such as diabetic, pressure, or venous insufficiency ulcers), flaps, and grafts. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

The term "topical" application refers to application to skin, dermis or tissue site, and application to such tissue sites may include application adjacent to or within the tissue site.

The term "bioactive composition" or "biologically active composition" as used herein refers to a composition formulated with at least one sacrificial proteolytic enzyme substrate and at least one antimicrobial agent. Such compositions may be formulated in any carrier or pharmaceutically acceptable carrier and will typically comprise an effective amount of sacrificial proteolytic enzyme substrate and antimicrobial agent to reduce inflammation and stimulate tissue healing.

The compositions disclosed herein are bioactive or biological compositions comprising or consisting essentially of one or more sacrificial proteolytic enzyme substrates, one or more preservatives, and one or more antimicrobial agents. The term "consisting essentially of" as used herein functions to limit the scope to the specified materials or steps as well as those that do not materially affect the basic and novel characteristic(s) of the claimed compositions or methods. In one embodiment, the compositions comprise or consist essentially of a MMP substrate as the sacrificial proteolytic enzyme substrate, EDTA as one of the preservatives, sodium benzoate as a second preservative, and one or more antimicrobial agents. The compositions may include one or more carriers and/or other inert agents that do not materially affect the basic and novel characteristics of the composition.

The term "carrier" as used herein refers to diluents, adjuvants, excipients, vehicles, and other inert agents with which the sacrificial proteolytic enzyme substrate is administered.

Described herein are compositions consisting of one or more sacrificial proteolytic enzyme substrate, one or more preservatives, and one or more antimicrobial agents. As an example, the composition consists of a MMP substrate as the sacrificial proteolytic enzyme substrate, EDTA and sodium benzoate as the preservatives, and one or more antimicrobial agents.

The compositions provided herein also include pharmaceutical compositions. The pharmaceutical compositions may include one or more pharmaceutically acceptable carriers and/or other pharmaceutically acceptable inert agents. The term "pharmaceutically acceptable" as used herein refers to ingredients, agents, or compositions that are suitable for pharmaceutical administration without undue toxicity, incompatibility, instability, irritation, allergic response and the like. A "pharmaceutically acceptable salt" can be derived from pharmaceutically acceptable inorganic or organic bases and from pharmaceutically acceptable inorganic and organic acids, which are known in the art and can be derived by one of ordinary skill in the art. Examples of pharmaceutically acceptable carriers include but are not limited to sugars, starches, cellulose, excipients, oils, glycols, polyols, esters, agar, and buffering agents. The above are non-limiting examples of carriers. Pharmaceutically acceptable carriers may be distinct from carrier materials described below and are known in the art. Pharmaceutically acceptable carriers other than those listed herein may be easily formulated by those of ordinary skill in the art.

The compositions disclosed herein may additionally comprise conventional adjuvants such as propionic acid, propylene glycol, conventional buffers, preservatives, hydrophilic emulsifiers, lipophilic emulsifiers, perfumes, emollients, deodorants, humectants and the like. Colorants may also optionally be added in the compositions disclosed herein. Adjuvants which would be harmful to a tissue site or surrounding skin should be avoided, as well as those adjuvants which may react with and/or adversely reduce the effectiveness of the composition.

The compositions disclosed herein may be formulated into a wide variety of articles to be topically applied that include but are not limited to lotions, creams, gels, sticks, sprays, ointments, pastes, foams, powders and film-forming products. The compositions provided herein may be formulated for debriding, irrigating, moisturizing, cleansing, lubricating, and/or disinfecting a tissue site. The composition may be a liquid formulation or in the form of a solution. Such compositions may be formulated for time-controlled release.

The compositions may be an instillation composition. The compositions may be delivered to a tissue site by continuous instillation and/or periodic instillation. The instillant provides fresh sacrificial proteolytic enzyme substrate, such as MMP substrate, and antimicrobial agent to the tissue site.

The compositions provided herein comprise sacrificial proteolytic enzyme substrates for preventing activation of an enzyme. As discussed above, normal endogenous levels of MMPs are essential for tissue remodeling during the healing process. However, in excess, they continually break down the new tissue that is formed. This leads to a wound that either does not heal quickly or becomes stalled. Excess levels of MMPs create a sustained state of inflammation thereby preventing the progression of normal wound healing. Accordingly, in certain aspects, methods are described herein for promoting healing or growth of tissue, comprising providing a composition containing a MMP substrate in an amount effective to reduce the level of MMPs and/or reduce inflammation at a tissue site and in surrounding tissue. Excessive MMP activity at a tissue site can also be addressed by providing a composition comprising a sacrificial proteolytic enzyme substrate, such as protein, protein hydrolysate, or combinations thereof.

The compositions provided herein comprise one or more substrates for MMP as the sacrificial proteolytic enzyme substrate. Examples of MMP substrates include, but are not limited to, collagen, gelatin, elastin, casein, albumin, fibrinogen, fibronectin, and combinations and hydrolysates thereof. In certain embodiments, proteins for use as sacrificial substrates are hydrolyzed or partially hydrolyzed by treatment with a strong acid or base. Such treatment can fragment the subject proteins and generate a more accessible peptide sequence to bind to proteolytic enzymes.

The compositions disclosed herein comprise about 0.01% to 25%, 0.01% to 10%, 0.03% to 1%, 0.03% to 5%, or 1% to 10% w/v, or about 6%, 8%, 10%, 15% or 20% w/v of sacrificial proteolytic enzyme substrate.

The most prevalent MMPs in chronic wounds are the gelatinase proteases, MMP-2 and MMP-9 that more readily target the hydrolyzed or denatured form of collagen known as "gelatin." Thus, in certain aspects, a bioactive composition for use as described here further comprises a collagen, such as a hydrolyzed collagen (e.g., gelatin). Gelatin can be processed from a variety of sources including, but not limited to, bovine skin, porcine skin and bone material. Depending on the hydrolysis methods employed in manufacture, the gelatin may be defined as a type A or type B gelatin. One advantage of using a gelatin rather than, or in addition to, collagen is that gelatin includes exposed peptide sequences that serve as signals for protease binding. Accessibility of signaling sequences in the native collagen molecule is diminished due to the triple-helix structure of the native collagen molecule, where polypeptide chains are bound with strong hydrogen bonds. Thus, in certain aspects, a composition is defined as not comprising collagen. In the case of gelatin, on the other hand, signaling sequences are readily exposed to proteases making it more efficient as a sacrificial substrate.

A primary constraint against using gelatin in wound dressings has been insufficient mechanical integrity and inability to maintain dressing shape in the wound environment as is possible with natural collagen. However, if gelatin is applied as a coating onto another porous material, such as a bandage, gauze, or polyurethane foam, which will provide structural support, such material with gelatin may be an excellent choice as a MMP sacrificial substrate. Therefore, in one embodiment, gelatin for use in the bioactive solution compositions provided herein can comprise a molecular weight of between about 2000 Da to about 20,000 Da or having a bloom value of less than about 150. In certain embodiments, it may be beneficial to use gelatin with sufficient gel strength (for example, a gelatin having a molecular weight of about 2000 Da to about 20,000 Da or having a bloom value of less than about 150) to form an adherent layer on a porous material without causing the material to become overly stiff.

Additionally, gelatin is an excellent oxygen barrier, which is important for stability of molecules that could be incorporated in wound dressings for instance, such as antioxidants and oxygen-sensitive proteins and peptides. Thus, the carrier material within a wound dressing may be a polyurethane foam as described herein that is coated with gelatin to provide the reduced pressure dressing with a sacrificial substrate for MMPs. The compositions may comprise, for example, 0.01% to 25%, 0.01% to 10%, 0.03% to 1%, 0.03% to 5%, or 0.5% to 10% w/v, or about 1%, 2%, 3%, 4% or 5% w/v of gelatin. The compositions may also comprise, for example, 0.1% to 25%, 1% to 10% or about 6%, 8%, 10%, 15%, or 20% w/w gelatin.

The compositions provided herein may include one or more preservatives. The compositions may contain preservatives for the MMP substrate. Examples of preservatives include, but are not limited to chelators such as EDTA, diethylene triamine pentaacetic acid (DTPA), and catechins; sodium benzoate; potassium sorbate; and sodium nitrate. EDTA is also capable of reducing MMP, and sodium benzoate works synergistically with EDTA. The compositions may comprise about 0.01% to about 5%, 0.1% to 3%, 0.015% to 1%, 0.015% to 0.5%, 0.01% to 0.1%, or 0.0225% to 0.1% w/v or about 0.015%, 0.225%, or 0.1% w/v.

The compositions provided herein comprise one or more antimicrobial agents. The antimicrobial agents can act to counter any bacterial protease activity that may hamper the healing environment, which allows a tissue site to progress towards an optimal healing state. Examples of antimicrobial agents include, but are not limited to, components of aloe vera, ashitaba, bacteriophage, beta-defensin, quaternary ammonium compound, chlorhexidine, copper, dispersin B, essential oil, gentamicin, lactoferrin, lysostaphin, N-halamines, nitric oxide, oleic acid, PLUNC, polyhexanide biguanide (PHMB), bacteriocin, selenium, silver compound, triclosan, zinc, and combinations thereof. Aloe vera contains numerous photochemical compounds including but not limited to tannin, saponin, flavonoids, and fumaric acid. As used herein, the term "PLUNC" refers to the gene or clone encoding the palate, lung, nasal epithelium carcinoma associated protein and to the protein itself. Examples of quaternary ammonium compound include benzethonium chloride and benzalkonium chloride. An example of a beta-defensin is cathelicidin (LL-37). Examples of a silver compound may include colloidal silver, ionic silver, nonionic silver, silver chloride, silver nanoparticles, and silver sulfadiazine. Examples of essential oil include but are not limited to cinnamon oil, clove oil, eucalyptus oil, and tea tree oil. An example of chlorhexidine is chlorhexidine gluconate. The compositions may comprise about 0.01% to 1%, 0.05% to 1%, or 0.05% to 0.5% w/v of antimicrobial agents.

The compositions disclosed herein may further comprise other agents such as growth factors, cytokines, and proteinase inhibitors, in particular proteinase inhibitors of MMPs. The compositions provided herein may consist essentially of or consist of one or more MMP substrates, one or more preservatives, one or more antimicrobial agents, one or more growth factors, and one or more proteinase inhibitors.

In certain aspects, the composition is sterilized by irradiation. A skilled worker will recognize that such irradiation can alter the amount of cross-linking within proteins in the composition. Thus, in cases where the composition comprises a sacrificial proteolytic enzyme substrate, such as a MMP substrate, that is a protein, such as gelatin, the amount of irradiation may be limited to prevent protein cross-linking, while still achieving sterilization.

In one embodiment, application of the composition provided herein may be infusion within, injection into, absorption by, layering on, encapsulation within, or coating on, a carrier material, such as a bandage, gauze, wound dressing, adhesive bandage, scaffold, or hydrogel. A "carrier material" as used herein refers to a material suitable for having a proteolytic enzyme substrate, such as a MMP substrate and an antimicrobial agent. For example, a composition of a proteolytic enzyme substrate and an antimicrobial agent may be applied to a woven, non-woven, or knitted fabric material, such as gauze, dispersed within film, sponge, or foam for sustained release at a tissue site. The carrier material may be either bioresorbable, for instance comprising polyglycolic acid, polylactic acid, polydioxanone, polyhydroxybutyrate, polyhydrozyvalerate, polyaminoacids polyorthoesters, polyvinyl alcohol, collagen, gelatin, chitosan, oxidized regenerated cellulose, hyaluronic acid, alginate or derivatives thereof, or may be non-bioresorbable, comprising for instance, polyurethane, polyvinyl alcohol, or gauze. In some embodiments, the carrier material may be made of the same substance as the proteolytic enzyme substrate, for instance collagen or a modified collagen, such as gelatin. Carrier materials are distinct from the carriers and pharmaceutically acceptable carriers used in bioactive compositions.

Suitable carrier materials include, but are not limited to: bandages, gauze, wound dressings, adhesive bandages, scaffold, hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols) as well as gelatin. The above carrier materials may include alginate (as a thickener or stimulant), buffers to control pH such as disodium hydrogen phosphate/sodium dihydrogen phosphate, agents to adjust osmolarity such as sodium chloride, and stabilizers such as EDTA.

The compositions provided herein are useful for the treatment of a tissue site by any method where the composition contacts the tissue site. For instance, the composition may contact a tissue site through direct application of a cream, a gel, an ointment or a spray. In another embodiment, the composition may be applied to a carrier material, which is then applied to a tissue site. Such methods may include application of the composition to a bandage, gauze, or dressing to be applied to a tissue site. The compositions provided herein may also be added to other known compositions for treating wounds or other tissue sites.

Also described herein are methods of using the disclosed composition for treating a tissue site by debriding, irrigating, moisturizing, cleansing, lubricating, and/or disinfecting the tissue site. The composition can deliver agents, including MMP substrates, antimicrobials, or growth factors, for example, to a tissue site, and can deliver such agents in a manner and/or sequence to debride eschar, necrotic tissue, and debris; cleanse, irrigate, moisturize, disinfect, and remove/reduce wound bioburden and microbial biofilms; retard microbial and biofilm regrowth; decrease pain, odor, inflammation; and promote wound healing physiology. The composition delivered to a tissue site can provide a moist environment to promote healing.

For example, the bioactive compositions presented herein may be integrated with negative pressure wound therapy (NPWT), fluid instillation therapy, or both. Clinical studies and practice have shown that NPWT can augment and accelerate growth of new tissue at a tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as NPWT, but is also known by other names, including "negative-pressure therapy," "reduced-pressure wound therapy," "vacuum therapy," and "vacuum-assisted closure," for example. Negative-pressure therapy may provide a number of benefits, including migration of epithelial and subcutaneous tissues, improved blood flow, and micro-deformation of tissue at a tissue site. Together, these benefits can increase development of granulation tissue and reduce healing times.

Instillation of a tissue site, which generally refers to the slow introduction of a solution to the tissue site, can expose a tissue site to temperature variations, drugs, or other substances that may further promote healing or growth of tissue. Instillation may also be referred to as irrigation or infusion in some contexts. Instillation may be continuous or intermittent and may take place prior to, subsequent to, or simultaneously with the application of negative pressure. In some embodiments, instillation and negative pressure may be coordinated by a central controller.

FIG. 1 is a simplified functional block diagram of an example embodiment of a therapy system 100 that can provide therapeutic pressure and instillation in accordance with this specification. As illustrated, the therapy system 100 may include a dressing 102 fluidly coupled to a negative-pressure source 104. A regulator or controller, such as regulator 106, may also be fluidly coupled to the dressing 102 and the negative-pressure source 104. The dressing 102 generally includes a drape, such as drape 108, and a manifold, such as distribution manifold 110. The therapy system 100 may also include fluid containers, such as container 112 and container 114, coupled to the dressing 102. As illustrated in FIG. 1, container 112 may be also be fluidly coupled to the negative-pressure source 104 in some embodiments, and container 114 may be coupled to a fluid-delivery device, such as a pump 116.

In general, components of the therapy system 100 may be coupled directly or indirectly. For example, the negative-pressure source 104 may be directly coupled to regulator 106 and indirectly coupled to dressing 102 through regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumens adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the distribution manifold 110 may be placed within, over, on, or otherwise proximate to a tissue site. The drape 108 may be placed over the distribution manifold 110 and sealed to tissue proximate to the tissue site. The tissue proximate to the tissue site is often undamaged epidermis peripheral to the tissue site. Thus, the dressing 102 can provide a sealed therapeutic environment proximate to a tissue site, substantially isolated from the external, ambient environment. The negative-pressure source 104 can reduce the pressure in the sealed therapeutic environment, and the pump 116 can apply therapeutic solutions, including the embodiments of the bioactive compositions described herein. Reduced pressure and/or fluids can be applied substantially uniformly through the distribution manifold 110 in the sealed therapeutic environment. Reduced pressure can induce macrostrain and microstrain in the tissue site, as well as remove exudate and other fluids from the tissue site, which can be collected in the container 112 and disposed of properly.

Integrating negative pressure therapy and instillation therapy with embodiments of bioactive compositions described herein can further promote healing and growth of tissue by removing barriers to normal healing, such as abnormally high levels of MMPs. To further promote healing and growth of tissue, embodiments of bioactive compositions including a preservative such as a chelator like EDTA and an antimicrobial agent, may work synergistically to kill microbes while preventing further biofilm formation. Functionally coupling infusion of the compositions with NPWT as disclosed herein provides unexpected decreases in wound bioburden and wound healing trajectories. The ability of a gelatin-based solution to operate with a NPWT system allows for the use of the solution as an instillate to cleanse a tissue site, in particular a chronic wound, with bioactive and antimicrobial agents.

In some embodiments, the negative pressure with the bioactive composition can be applied during debridement of a tissue site. Alternatively, negative pressure therapy may be applied after debridement, to promote vascular stimulation and the formation of granulation tissue. Further still, the transition from debridement to negative pressure therapy is seamless, as well as from negative pressure therapy to passive infusion with the composition, that is, without disrupting the integrity of the tissue site.

The negative pressure with the bioactive composition may also be applied during cleansing or irrigation of the wound in some embodiments. Alternatively, the negative pressure may be applied prior to or after the cleansing of the wound with the composition.

The compositions provided herein can be used in conjunction with all current NPWT devices, and delivered in either the inpatient or outpatient setting. Exemplary negative pressure devices include V.A.C.® Therapy, V.A.C. Instill®, or V.A.C. Ulta® therapy systems (Kinetic Concepts, Inc.). These devices or devices having similar or equivalent designs may be used.

"Negative pressure" or "reduced pressure" generally refers to a pressure less than a local ambient pressure, such as the ambient pressure in a local environment external to a sealed therapeutic environment provided by the dressing 102. In many cases, the local ambient pressure may also be the atmospheric pressure in the vicinity of a tissue site. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A negative-pressure source, such as the negative-pressure source 104, may be a reservoir of air maintained at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

A fluid-delivery device, such as the pump 116, may be a rotary-delivery pump, or other pump that can supply an instillation solution to a sealed space or the distribution manifold 110. A fluid-delivery device may be housed within a therapy device or used in conjunction with other components, such as sensors, processing units, alarm indicators, memory, databases, software, display devices, or user interfaces that further facilitate instillation therapy. In some embodiments, a fluid-delivery device and a negative-pressure source may be integrated into a single unit to provide both negative pressure and instillation, or to alternatingly supply negative pressure and instillation.

A manifold, such as the distribution manifold 110, can generally be adapted to contact a tissue site. The distribution manifold 110 may be adapted to be placed partially or fully in contact with the tissue site. If the tissue site is a wound, for example, the distribution manifold 110 may partially or completely fill the wound, or may be placed over the wound. The distribution manifold 110 may take many forms, and may be many sizes, shapes, or thicknesses depending on a variety of factors, such as the type of treatment being implemented or the nature and size of a tissue site. For example, the size and shape of the distribution manifold 110 may be adapted to the contours of deep and irregular shaped tissue sites.

More generally, a manifold is a substance or structure adapted to distribute negative pressure to or remove fluids from a tissue site, or both. In some embodiments, though, a manifold may also facilitate delivering fluids to a tissue site, if the fluid path is reversed or a secondary fluid path is provided, for example when instillation solution is applied. A manifold may include flow channels or pathways that distribute fluids provided to and removed from a tissue site around the manifold. In one illustrative embodiment, the flow channels or pathways may be interconnected to improve distribution of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In one illustrative embodiment, the distribution manifold 110 may be a porous foam material having interconnected cells or pores adapted to uniformly (or quasi-uniformly) distribute reduced pressure to a tissue site. The foam material may be either hydrophobic or hydrophilic. In one non-limiting example, the distribution manifold 110 may be an open-cell, reticulated polyurethane foam such as Granu-Foam® dressing available from Kinetic Concepts, Inc. of San Antonio, Tex.

In some embodiments, such as embodiments in which the distribution manifold 110 may be made from a hydrophilic material, the distribution manifold 110 may also wick fluid away from a tissue site while continuing to distribute reduced pressure to the tissue site. The wicking properties of the distribution manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 110 may further promote granulation at a tissue site if pressure within a sealed therapeutic environment is reduced. For example, any or all of the surfaces of the distribution manifold 110 may have an uneven, coarse, or jagged profile that can induce microstrains and stresses at a tissue site if reduced pressure is applied through the distribution manifold 110.

In one example embodiment, the distribution manifold 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and caprolactones.

Other bioresorbable materials that may be used include, but are not limited to, polydioxanone, polyhydroxybutyrate, polyhydrozyvalerate, polyaminoacids polyorthoesters, polyvinyl alcohol, chitosan, oxidized regenerated cellulose, hyaluronic acid, alginate, collagen, a modified collagen, such as gelatin or derivatives of any of the above.

The distribution manifold 110 may further serve as a scaffold for new cell-growth, or a scaffold material may be used in conjunction with the distribution manifold 110 to promote cell-growth. In general, a scaffold material may be a substance or structure used to enhance or promote the growth of cells or formation of tissue, such as a three-dimensional porous structure that provides a template for cell growth.

A scaffold and/or manifold may be also be infused with, coated with, or comprised of cells, growth factors, extracellular matrix components, nutrients, integrins, or other substances to promote cell growth in addition to embodiments of the compositions described herein. The manifold or scaffold may serve as a carrier material for the composition described herein.

Scaffolds may be formed from biologic or synthetic scaffold materials, and are used in the field of tissue engineering to support protein adhesion and cellular ingrowth for tissue repair and regeneration. The current state of the art in scaffold technology relies upon the inherent characteristics of the surrounding tissue space for the adsorption of proteins and migration of cells. Nonlimiting examples of suitable scaffold materials include extracellular matrix proteins such as fibrin, collagen or fibronectin, and synthetic or naturally occurring polymers, including bioabsorbable or non-absorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes (e.g., GranuFoam®), polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon.

The scaffold can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In some embodiments, the scaffold may comprise collagen (e.g., Biostep® or Promogran® scaffolds), polylactic acid (PLA), polyglycolic acid (PGA), polylactide-co-glycolide (PLGA), a polyurethane, a polysaccharide, an hydroxyapatite, or a polyether-ylene glycol. Additionally, the scaffold can comprise combinations of any two, three or more materials, either in separate or multiple areas of the scaffold, combined noncovalently or covalently (e.g., copolymers such as a polyethylene oxide-polypropylene glycol block copolymers, or terpolymers), or combinations thereof.

The drape 108 is an example of a sealing member. A sealing member may be constructed from a material that can provide a fluid seal between two environments or components, such as between a therapeutic environment and a local external environment. The sealing member may be, for example, an impermeable or semi-permeable, elastomeric material that can provide a seal adequate to maintain a negative pressure at a tissue site for a given negative-pressure source. For semi-permeable materials, the permeability generally should be low enough that a desired negative pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The container 114 is representative of another container, canister, pouch, cartridge, or other storage component, which can be used to manage instillation solution to be supplied to a tissue site. In many environments a rigid container may be preferred or required for delivering, storing, and supplying of the instillation solution. In other environments, instillation solution may be provided in a non-rigid container, and a re-usable container could reduce waste and costs associated with instillation.

Components of therapy system 100 may also be provides as one or more kits. In one embodiment, for example, a kit comprises the system described above and one or more embodiments of a bioactive composition described herein. In another embodiment, a kit comprises one or more embodiments of a bioactive composition described herein and an apparatus for delivering the composition to a tissue site. The apparatus may include a dressing.

The systems and methods described herein may provide significant advantages, some of which have already been mentioned. For example, the compositions, apparatuses, methods, systems, and kits described herein can enable the delivery of agents to tissue sites that may not have been reachable with a conventional collagen dressing, since a liquid based solution follows a path of least resistance. Moreover, moisture and MMP scavenging can be maintained at a tissue site. The added antimicrobial activity to the compositions described herein can also provide bacterial killing ability and reduce proteolytic activity. The viscosity and the adhesive nature of the gelatin enhance these effects.

EXAMPLES

The following examples are included to demonstrate the advantages and unexpected results of certain embodiments. Those of skill in the art should, in light of the present disclosure, appreciate that many changes can be made to the specific embodiments which are disclosed and still obtain a like or similar result without departing from the scope of the claims. More specifically, it will be apparent that certain agents, which are both chemically and physiologically related, may be substituted for the agents described herein while the same or similar results would be achieved. All such similar substitutes and modifications apparent to those skilled in the art are deemed to be within the scope of the appended claims.

Example 1

Gelatin Instillant Wound Cleanse Solution

Gelatin solution was prepared by dissolving gelatin in water to make a 50 mg/mL stock solution. Serial dilutions were made by mixing the stock solution with additional water. A stock MMP-9 proenzyme was activated with APMA per a method suggested by the enzyme manufacturer. Activated proenzyme is diluted to the appropriate concentration in assay buffer. MMP-9 and gelatin solutions are added in specific quantities (determined by desired concentration of each) to each assay well.

MMP-9 activity is measured by reading a colorimetric reaction which results from hydrolysis of a thioester bond by active MMP-9 resulting in production of a sulfhydryl group which then reacts with Ellman's reagent. Higher absorbance readings correlate to higher MMP-9 activity.

Figure 2:
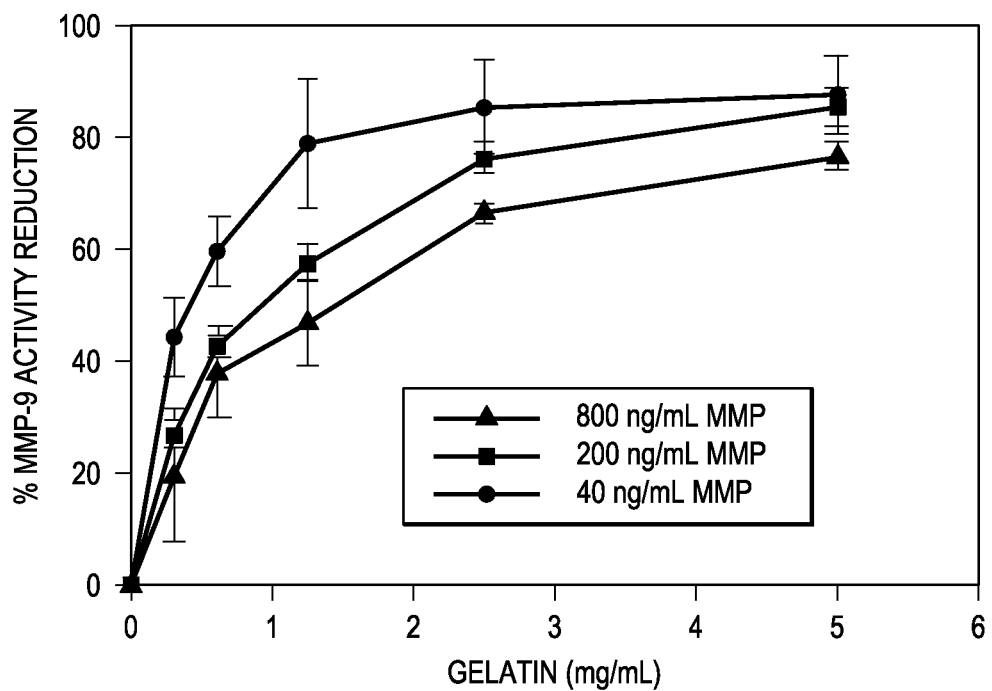
FIG. 2 shows the ability of an embodiment of the bioactive composition described herein to competitively inhibit MMP-9 activity at three different enzyme protein concentrations.

FIG. 2 shows the ability of gelatin solution to competitively inhibit MMP activity at three different enzyme protein concentrations.

Example 2

Performance of Gelatin Solution with NPWTi

The V.A.C. Veraflo® dressing was placed on a sheet of 0.5 inch thick acrylic approximately 3 inch×3 inch square shaped and covered utilizing V.A.C. Veraflo® advanced drape. Therapy was set to Instill with instillation volume set at 35 cc with a soak time of 10 minutes. Therapy time was 3.5 Hours at −125 mmHg. Data points were then read across a 36-manometer pad and averaged as seen in FIG. 3.

The gelatin solution performs with the V.A.C. ULTA®, a NPWTi system from Kinetic Concepts, Inc., with high similarity to a normal saline solution. FIG. 3A and FIG. 3B show the distribution of pressure with the gelatin solution and with normal saline. As shown, there is no degradation of negative pressure after the system stabilizes from the instill cycle. FIGS. 3A and 3B only show initial peaks up to the 1000 second time point as the system stabilizes.

Although the present invention and its advantages have been disclosed in the context of certain illustrative, non-limiting embodiments, it should be understood that various changes, substitutions, permutations, and alterations can be made without departing from the scope of the invention as defined by the appended claims.

The invention claimed is:

1. A method of treating a tissue site, comprising:
   delivering via instillation a composition in a dispensable liquid form to the tissue site, wherein the composition comprises:
      one or more matrix metalloprotease (MMP) substrates, wherein the MMP substrates comprise gelatin or a hydrolysate thereof,
      one or more preservatives comprising a chelating agent, wherein the chelating agent is ethylenediaminetetraacetic acid (EDTA), and
      a pharmaceutically-acceptable carrier; and
   applying negative pressure to the tissue site to remove at least a portion of the composition delivered to the tissue site.

2. The method of claim 1, wherein the tissue site is treated with the composition prior to applying negative pressure.

3. The method of claim 1, wherein the tissue site is treated with the composition after applying negative pressure.

4. The method of claim 1, wherein the tissue site is treated with the composition while applying negative pressure.

5. The method of claim 1, wherein the method further comprises applying a dressing to the tissue site, wherein the dressing is connected to a pressure source for applying negative pressure to the tissue site, and wherein the composition flows through the dressing to the tissue site.

6. The method of claim 5, wherein the dressing comprises an open-cell reticulated polyurethane foam pad.

7. The method of claim 6, wherein the method further comprises treating the foam pad with the composition prior to use.

8. The method of claim 7, wherein the foam pad is infused and coated on the surface with the composition.

9. The method of claim 6, wherein the method comprises continuous instillation of the composition to the tissue site.

10. The method of claim 6, wherein the method comprises periodic instillation of the composition to the tissue site.

11. The method of claim 1, wherein the method of treating the tissue site comprises continuous instillation of the tissue site with the composition.

12. The method of claim 1, wherein the method of treating the tissue site comprises periodic instillation of the tissue site with the composition.

13. The method of claim 1, wherein the composition further comprises one or more antimicrobial agents.

14. The method of claim 1, wherein the composition further comprises one or more growth factors.

15. The method of claim 1, wherein the composition further comprises one or more proteinase inhibitors.

16. The method of claim 1, wherein the gelatin comprises a molecular weight of between 2000 Da to 20,000 Da.

17. The method of claim 1, wherein the gelatin has a bloom value of less than 150.

18. The method of claim 1, wherein the one or more preservatives further comprises sodium benzoate.

19. A system for treating a tissue site, the system comprising:
   a negative-pressure source;
   a container adapted to contain a composition, wherein the composition comprises:
      one or more matrix metalloprotease (MMP) substrates, wherein the MMP substrates comprise gelatin or a hydrolysate thereof,
      one or more preservatives comprising a chelating agent, wherein the chelating agent is ethylenediaminetetraacetic acid (EDTA), and
      a pharmaceutically-acceptable carrier;
   a dressing in fluid communication with the negative-pressure source and adapted to distribute negative pressure to the tissue site, wherein the dressing has a first portion adapted for contact with the tissue site, and a second portion in fluid communication with the container;
   a pump adapted to deliver the composition to the dressing; and
   a drape adapted to cover the dressing.

20. The system of claim 19, wherein the dressing is infused and coated with the composition.

21. The system of claim 19, wherein the composition further comprises one or more antimicrobial agents, one or more growth factors, and one or more proteinase inhibitors that are proteinase inhibitors of MMPs.

22. The system of claim 21, wherein the composition is a solution.

23. The system of claim 22, wherein the one or more preservatives comprises sodium benzoate, potassium sorbate, or sodium nitrate.

24. The system of claim 19, wherein the dressing comprises an open-cell reticulated polyurethane foam pad.

25. The system of claim 24, wherein the foam pad is treated with the composition prior to use.

26. The system of claim 25, wherein the foam pad is infused and coated on the surface with the composition.

27. The system of claim 19, wherein the gelatin comprises a molecular weight of between 2000 Da to 20,000 Da.

28. The system of claim 19, wherein the gelatin has a bloom value of less than 150.

29. The system of claim 19, wherein the one or more preservatives further comprises sodium benzoate.

30. The system of claim 19, wherein the composition is provided in a dispensable liquid form for instillation to the tissue site.

31. A method of delivering a composition consisting essentially of one or more matrix metalloprotease (MMP) substrates comprising gelatin or a hydrolysate thereof, one or more preservatives comprising a chelating agent comprising ethylenediaminetetraacetic acid (EDTA), and a pharmaceutically acceptable carrier, and optionally further comprising a component selected from the group consisting of a proteinase inhibitor, an antimicrobial agent, a growth factor, and combinations thereof; wherein the composition is provided in a dispensable liquid form for instillation to a tissue site.

32. The method of claim 31, wherein the antimicrobial agent comprises polyhexanide biguanide (PHMB).

33. The method of claim 31, wherein the gelatin comprises a molecular weight of between 2000 Da to 20,000 Da.

34. The method of claim 31, wherein the gelatin has a bloom value of less than 150.

35. The method of claim 31, wherein the one or more preservatives further comprises sodium benzoate.

\* \* \* \* \*